US008492604B2

(12) United States Patent
Fritz et al.

(10) Patent No.: US 8,492,604 B2
(45) Date of Patent: Jul. 23, 2013

(54) METHOD FOR PREPARING LINEAR ALPHA-OLEFINS WITH REMOVAL OF AROMATIC BY-PRODUCTS AND REACTOR SYSTEM THEREFOR

(75) Inventors: Peter M. Fritz, Unterhaching (DE); Wolfgang Müller, Munich (DE); Florian Winkler, Munich (DE); Heinz Bölt, Wolfratshausen (DE)

(73) Assignee: Saudi Basic Industries Corporation, Riyadh (SA)

( * ) Notice: Subject to any disclaimer, the term of this patent is extended or adjusted under 35 U.S.C. 154(b) by 635 days.

(21) Appl. No.: 12/225,395

(22) PCT Filed: Jan. 31, 2007

(86) PCT No.: PCT/EP2007/000812
§ 371 (c)(1),
(2), (4) Date: Mar. 28, 2011

(87) PCT Pub. No.: WO2007/107202
PCT Pub. Date: Sep. 27, 2007

(65) Prior Publication Data
US 2011/0178355 A1 Jul. 21, 2011

(30) Foreign Application Priority Data
Mar. 21, 2006 (EP) ..................... 06005686

(51) Int. Cl.
*C07C 7/152* (2006.01)
*C07C 2/66* (2006.01)

(52) U.S. Cl.
USPC ........... 585/809; 585/804; 585/466; 585/467; 585/462

(58) Field of Classification Search
USPC .......................... 585/809, 804, 466, 467, 462
See application file for complete search history.

(56) References Cited

FOREIGN PATENT DOCUMENTS

| DE | 4338414 C1 | 3/1995 |
| WO | WO 2004/072005 A | 8/2004 |

*Primary Examiner* — Thuan D Dang
(74) *Attorney, Agent, or Firm* — Cantor Colburn LLP

(57) ABSTRACT

The present invention relates to a method and a reactor system for preparing linear alpha-olefins by oligomerization of ethylene in the presence of an organic solvent and an oligomerization catalyst, wherein a product fraction of $C_{10+}$ alpha-olefins contaminated with aromatic $C_{9+}$ compounds is separated from a product main stream and transferred into a conversion reactor, where $C_{10+}$ alpha-olefins and aromatic $C_{9+}$ components are reacted in the presence of a Friedel-Crafts alkylation catalyst to produce aromatic $C_{19+}$ compound.

16 Claims, 1 Drawing Sheet

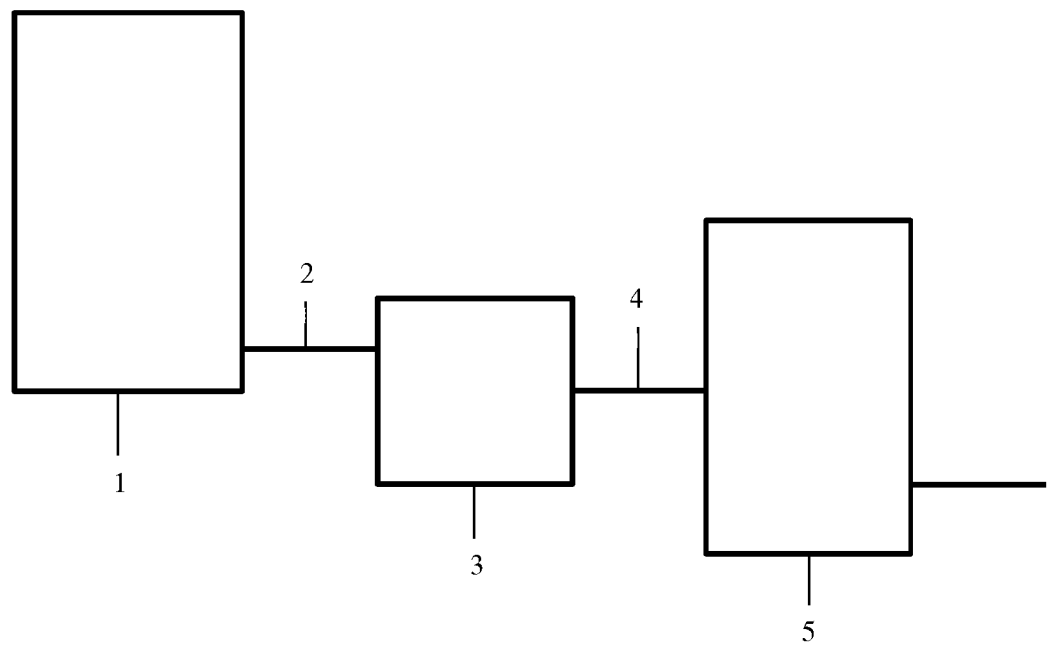

METHOD FOR PREPARING LINEAR ALPHA-OLEFINS WITH REMOVAL OF AROMATIC BY-PRODUCTS AND REACTOR SYSTEM THEREFOR

The present invention relates to a method for preparing linear alpha-olefins by oligomerization of ethylene in the presence of an organic solvent and a catalyst.

Methods for the production of linear alpha-olefins by oligomerization of ethylene are widely known in the art. Usually, a catalyst is utilized in that process comprising a zirconium component and an organoaluminum component which acts as an activator.

For example, DE 43 38 414 C1 discloses a process for the production of linear alpha-olefins, wherein one reactor is utilized into which a catalyst solution and ethylene are introduced. That process results in a product distribution of linear alpha-olefins having $C_4$-$C_{28}$; carbon atoms, wherein the fraction of $C_{20+}$ usually contains waxy, polymeric substances.

The product stream containing alpha-olefins with $C_4$-$C_{28}$ carbon atoms may be separated into fractions, e.g. by distillation or extraction. One main fraction obtained is a fraction containing $C_{10+}$ alpha-olefins, preferably $C_{10}$-$C_{18}$. This fraction may be often contaminated by aromatic components, preferably $C_{9+}$ aromatic components which are formed during oligomerization. Of course, these by-products are not desired, as a less valuable fraction $C_{10+}$ is provided. In the prior art, the aromatic components have been so far removed by repeated extraction and/or distillation, e.g. five distillation columns have been used so far to remove the aromatic components from the $C_{10+}$ alpha olefin fraction.

It is therefore an object of the present invention to provide a method for preparing linear alpha-olefins which overcomes the drawbacks of the prior art. Especially, a method shall be provided wherein aromatic by-products, commonly present in the $C_{10+}$ alpha-olefin fraction, can be easily removed with low costs, in order to improve the value of the $C_{10+}$ alpha-olefin fraction.

This object is achieved in that a product fraction of $C_{10+}$ alpha-olefins contaminated with aromatic $C_{9+}$ compounds is separated from a product main stream and transferred into a conversion reactor, where $C_{10+}$ alpha-olefins and aromatic $C_{9+}$ components are reacted in the presence of a Friedel-Crafts alkylation catalyst to produce aromatic $C_{19+}$ components.

Preferably, the Friedel-Crafts-alkylation catalyst is selected from any material with sufficient acidity to catalyze the alkylation.

More preferably, the Friedel-Crafts-alkylation catalyst is selected from clay, zeolites, Lewis acids and protonic acids.

In one preferred embodiment, the Friedel-Crafts-alkylation catalyst is selected from clay, zeolite, $H_2SO_4$, $P_4O_{10}$, $H_3PO_4$, $AlCl_3$, $FeCl_3$, $SbCl_5$, $SnCl_4$, $BF_3$, $TiCl_4$ and $ZnCl_2$.

The aromatic $C_{19+}$ compounds prepared may be preferably separated from unreacted $C_{10+}$ alpha-olefins in or downwards the conversion reactor, preferably by distillation.

Moreover, it is preferred that the separated $C_{19+}$ compounds are combined with $C_{20+}$ residue obtained during the oligomerization.

The aromatic $C_{19+}$ compounds may be transferred to a further device for thermal use thereof, preferably combustion.

In one preferred embodiment, the conversion in the conversion reactor is conducted at ambient temperature.

Further preferred, additional solvent is added to the fraction of $C_{10+}$ alpha-olefins prior to introduction into the conversion reactor.

Most preferably, the $C_{10+}$ alpha-olefin fraction is a $C_{10}$-$C_{18}$ fraction.

The invention further provides a reactor system for oligomerization of ethylene to form linear alpha-olefins, preferably utilizing a method according to the invention, comprising an oligomerization reactor and a conversion reactor, wherein a Friedel-Crafts-alkylation catalyst is present in that conversion reactor.

Surprisingly, it was found that the aromatic by-products contained in the $C_{10+}$ linear alpha-olefin fraction can be easily converted (removed) by reacting the $C_{10+}$ alpha-olefins with aromatic components, obtained in the oligomerization process, in the presence of a Friedel-Crafts alkylation catalyst in a separate conversion reactor to produce aromatic components having at least $C_{19+}$. These $C_{19+}$ aromatic components can be easily separated from the $C_{10+}$ alpha-olefin fraction and can be further processed, for example, combusted. Thus, the separation of the aromatic by-products is achieved in a very simple method step and safes five distillation columns which have been used so far to separate the aromatic by-products from the alpha-olefins fraction. Therefore, investment and operation costs are decreased, and a value added product (alpha-olefin fraction without by-products) is obtained.

As is obvious for someone skilled in the art, the concept of the present invention may be also adapted to any hydrocarbon streams containing aromatic impurities or by-products. For example, in case of paraffinic streams, olefins have to be added into the paraffinic stream to allow the conversion to heavy aromatic compounds which may be easily separated.

BRIEF DESCRIPTIONS OF THE DRAWING

Diagrammatic view of a reactor system for production of linear alpha olefin according to the present invention.

In general, the conversion of linear alpha-olefins ($C_{10+}$) with aromatic components ($C_{9+}$) is according to the following scheme:

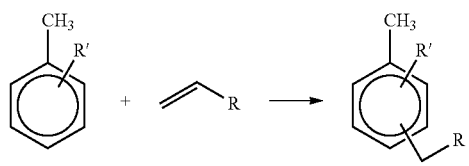

wherein R' is any alkyl group having two or more carbon atoms and R is any alkyl group having at least eight carbon atoms, preferably eight to sixteen carbon atoms.

Additional advantages and features of the inventive method and reactor system are further illustrated with reference to the accompanying drawing, wherein FIG. 1 illustrates a schematic diagram of the reactor system for carrying out the method according to the present invention.

In FIG. 1 a reactor 1 for the oligomerization of ethylene to prepare linear alpha-olefins is pro-vided. In the reactor 1 ethylene is oligomerized in the presence of a solvent, preferably toluene, and a suitable catalyst, preferably at a temperature of about 60-100° C. After oligomerization (the reactor is preferably operated continuously), a product stream is removed from the reactor via a discharge line 2. The product stream comprises the solvent, catalyst, liquid linear alpha-olefins and high molecular weight oligomers as well as unreacted dissolved ethylene. The constituents of the product stream may be separated, e.g. in a separation unit 3. For example, the liquid linear alpha-olefins may be separated into several fractions by distillation to obtain fractions of $C_4$-$C_8$, $C_{10}$-$C_{18}$ and $C_{20+}$. Usually, the fraction of $C_{10}$-$C_{18}$ ($C_{10+}$) comprises aromatic by-products. This fraction may be transferred from the separation unit 3 via line 4 into a conversion reactor 5, optional additional solvent may be provided, wherein the $C_{10+}$ fraction and the aromatic by-products are reacted in the presence of a Friedel-Crafts-allylation catalyst. The discharge stream of the conversion reactor 5 may be then further processed, e.g. the aromatic by-products (now $C_{19+}$) can be separated from the alpha-olefins by distillation and transferred to a further device, e.g. for combustion. The purified $C_{10+}$ fraction may be utilized for any desired purpose and has added value.

The features disclosed in the foregoing description, in the drawing or in the claims may, both separately and in any combination thereof, be material for realizing the invention in diverse forms thereof.

The invention claimed is:

1. A method for removing $C_{9+}$ aromatic compounds from the linear alpha-olefins product of the oligomerization of ethylene in the presence of an organic solvent and an oligomerization catalyst, comprising separating the linear alpha-olefins product into molecular weight fractions including at least a $C_{10+}$ alpha-olefins fraction which comprises $C_{10+}$ alpha-olefins and $C_{9+}$ aromatic compounds and then subjecting the $C_{10+}$ alpha-olefins fraction to an alkylation reaction wherein $C_{10+}$ alpha-olefins and the $C_{9+}$ aromatic compounds in the $C_{10+}$ alpha-olefins fractions are reacted in the presence of a Friedel-Crafts alkylation catalyst to produce $C_{19+}$ aromatic compounds.

2. The method according to claim 1, wherein the Friedel-Crafts alkylation catalyst is selected from materials with sufficient acidity to catalyze the alkylation reaction.

3. The method according to claim 2, wherein the Friedel-Crafts alkylation catalyst is selected from clay, zeolites, Lewis acids and protonic acids.

4. The method according to claim 2, wherein the Friedel-Crafts alkylation catalyst is selected from clay, zeolite, $H_2SO_4$, $P_4O_{10}$, $H_3PO_4$, $AlCl_3$, $FeCl_3$, $SbCl_5$, $SnCl_4$, $BF_3$, $TiCl_4$ and $ZnCl_2$.

5. The method according to claim 1, wherein the $C_{19+}$ aromatic compounds are separated from the $C_{10+}$ alpha-olefins fraction after the alkylation reaction.

6. The method according to claim 5, wherein the $C_{19+}$ aromatic compounds are separated from the $C_{10+}$ alpha-olefins fraction by distillation.

7. The method according to claim 3, wherein the $C_{19+}$ aromatic compounds are separated from the $C_{10+}$ alpha-olefins fraction after the alkylation reaction.

8. The method according to claim 7, wherein the $C_{19+}$ aromatic compounds are separated from the $C_{10+}$ alpha-olefins fraction by distillation.

9. The method according to claim 1, wherein the alkylation reaction is at ambient temperature.

10. The method according to claim 9, wherein solvent is added to the $C_{10+}$ alpha-olefins fraction prior to the alkylation reaction.

11. The method according to any of the preceding claims claim 1, wherein the $C_{10+}$ alpha-olefins fraction is comprises a $C_{10}$-$C_{18}$ alpha-olefins fraction.

12. The method according to claim 6, wherein the alkylation reaction is at ambient temperature.

13. The method according to claim 8, wherein the alkylation reaction is at ambient temperature.

14. The method according to claim 3, wherein solvent is added to $C_{10+}$ alpha-olefins fraction prior to the alkylation reaction.

15. The method according to claim 6, wherein the $C_{10+}$ alpha-olefins fraction is a $C_{10}$-$C_{18}$ alpha-olefins fraction.

16. The method according to claim 8, wherein the $C_{10+}$ alpha-olefins fraction is a $C_{10}$-$C_{18}$ alpha-olefins fraction.

\* \* \* \* \*